United States Patent [19]

Arai et al.

[11] Patent Number: 4,801,725

[45] Date of Patent: Jan. 31, 1989

[54] ORGANOSILICON COMPOUND

[75] Inventors: Masatoshi Arai; Shinichi Satoh; Kazutoshi Fujioka, all of Annaka, Japan

[73] Assignee: Shin-Etsu Chemical Co., Ltd., Tokyo, Japan

[21] Appl. No.: 92,000

[22] Filed: Sep. 2, 1987

[30] Foreign Application Priority Data

Sep. 4, 1986 [JP] Japan .................................. 61-208793

[51] Int. Cl.$^4$ .............................................. C07F 7/08
[52] U.S. Cl. ............................................ 556/434; 556/435
[58] Field of Search ................................. 556/435, 434

[56] References Cited

U.S. PATENT DOCUMENTS

| | | | |
|---|---|---|---|
| 3,109,013 | 10/1963 | Haluska | 556/434 X |
| 3,109,826 | 11/1963 | Smith | 556/434 X |
| 3,346,610 | 10/1967 | Omietanski et al. | 556/435 X |
| 3,798,252 | 3/1974 | Nitzsche et al. | 556/435 |
| 3,819,674 | 6/1974 | Rudolph et al. | 556/434 |

Primary Examiner—Paul F. Shaver

Attorney, Agent, or Firm—Foley & Lardner, Schwartz, Jeffery, Schwaab, Mack, Blumenthal & Evans

[57] ABSTRACT

An organosilicon compound represented by General Formula (I):

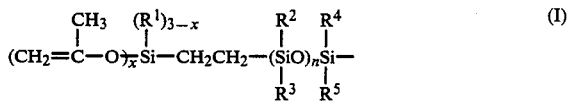

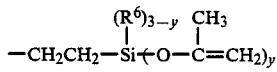

wherein $R^1$, $R^2$, $R^3$, $R^4$, $R^5$ and $R^6$ may be the same or different, and each represent a substituted or unsubstituted monovalent hydrocarbon group, x and y each represent an integer of 1 to 3, and n is an integer of 0 or more.

This compound is useful as a starting material for ultraviolet curable silicone compositions and room temperature curable silicone compositions.

3 Claims, 3 Drawing Sheets

ORGANOSILICON COMPOUND

BACKGROUND OF THE INVENTION

1. Field of the Invention

This invention relates to a novel organosilicon compound, and, particularly, to a novel organosilicon compound useful as a starting material for ultraviolet curable silicone compositions and room temperature curable silicone compositions.

SUMMARY OF THE INVENTION

An object of this invention is to provide a novel organosilicon compound useful as a starting material for ultraviolet curable silicone compositions and room temperature curable silicone compositions.

According to this invention, there is provided a novel organosilicon compound represented by General Formula (I):

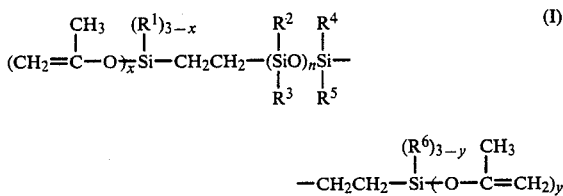

wherein $R^1$, $R^2$, $R^3$, $R^4$, $R^5$ and $R^6$ may be the same or different, and each represent a substituted or unsubstituted monovalent hydrocarbon group, x and y each represent an integer of 1 to 3, and n is an integer of 0 or more.

The organosilicon compound of this invention is a novel substance, and useful as a starting material for ultraviolet curable silicone compositions and room temperature curable silicone compositions.

DETAILED DESCRIPTION OF THE INVENTION

Figure 1:
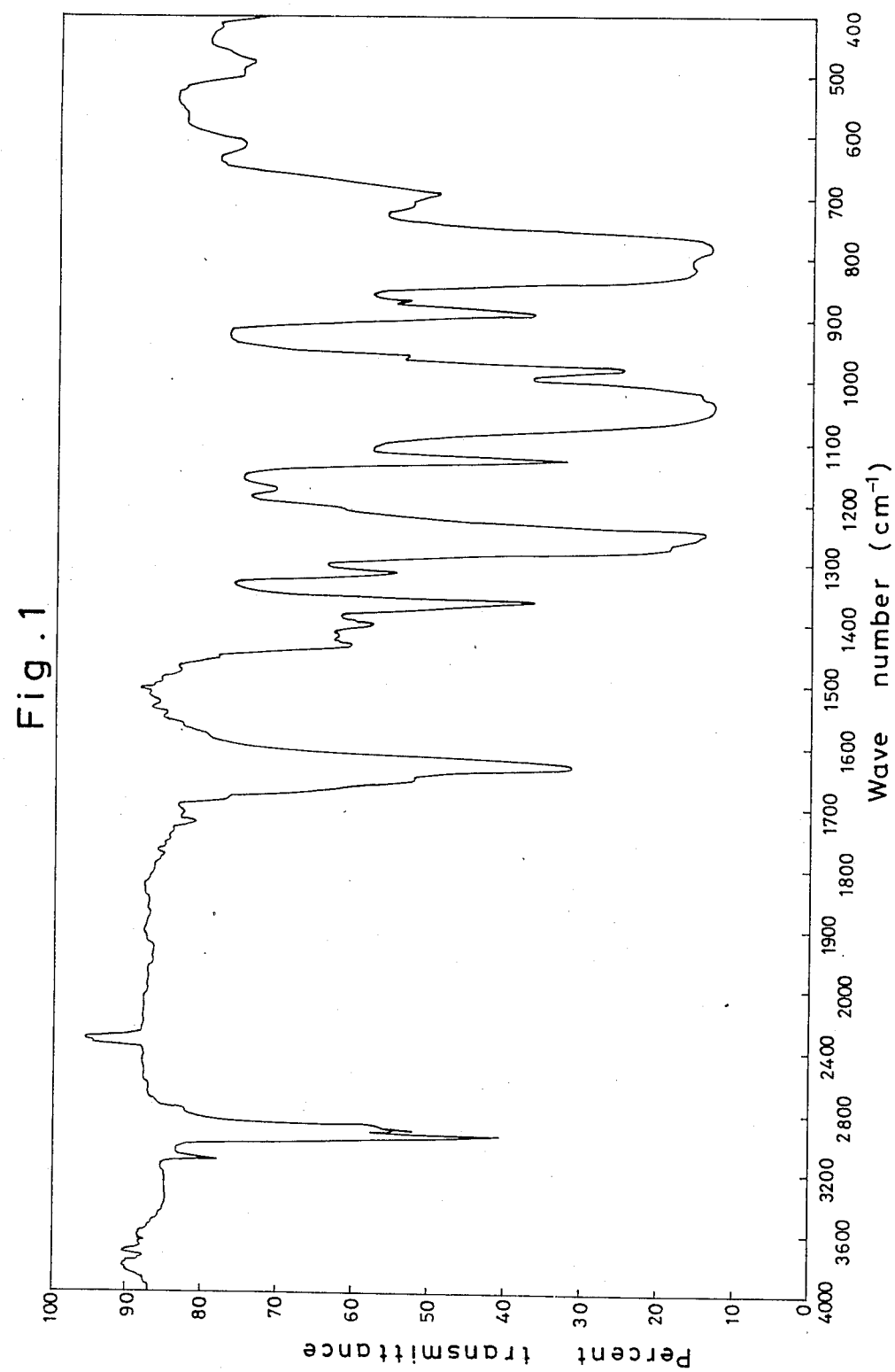
FIG. 1, FIG. 2 and FIG. 3 show IR spectra of organosilicon compounds of this invention.

The substituted or unsubstituted hydrocarbon group represented by $R^1$ to $R^6$ in General Formula (I) representing the organosilicon compound of this invention may include alkyl groups such as methyl, ethyl and propyl; alkenyl groups such as vinyl and allyl; alkynyl groups such as ethynyl; cycloalkyl groups such as cyclohexyl; aryl groups such as phenyl and tolyl; aralkyl groups such as benzyl; alkoxy groups such as methoxy and ethoxy; and those in which one or more, or, in a certain instance, all, of the hydrogen atom(s) possessed by any of these groups has or have been substituted with a halogen atom such as fluorine, chlorine and bromine, a cyano group, etc.

Typical examples of the organosilicon compound of General Formula (I) may include compounds in which $R^1$, $R^2$, $R^3$, $R^4$, $R^5$ and $R^6$ are selected from lower alkyl groups such as methyl, ethyl and propyl, and n is an integer of 0 to 2,000. Most typical examples are compounds in which $R^1$, $R^2$, $R^3$, $R^4$, $R^5$ and $R^6$ each is a methyl group and n is 1 to 1,000.

Examples of the organosilicon compound of General Formula (I) may include, for example, the following:

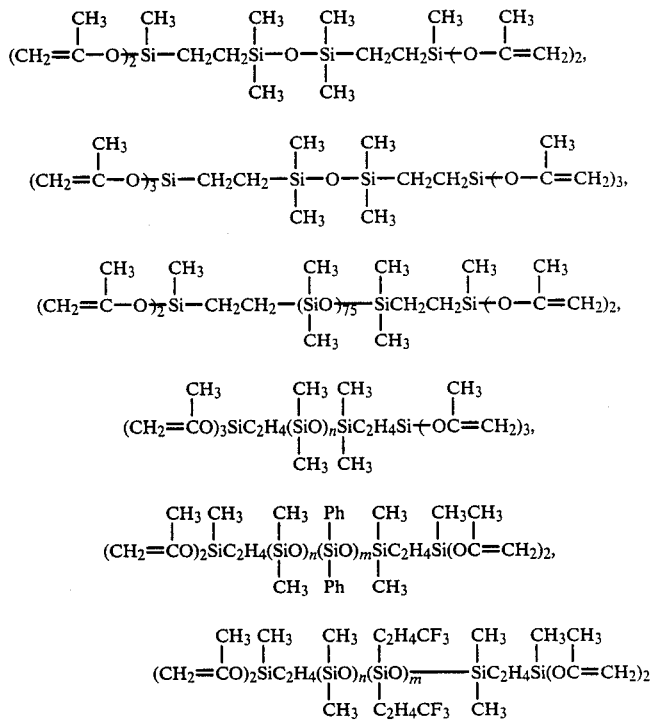

(In the above formulas, n represents an integer of 0 or more, and m represents an integer of one or more.)

Processes for synthesizing the compound represented by Formula (I) according to this invention may include, for example, a process in which a silane having silicon-bonded hydrogen atom (hereinafter called "hydrogen silane") represented by General Formula:

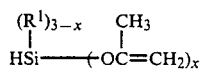 (II)

wherein R¹ and x are as defined above, for example,

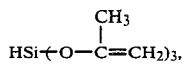

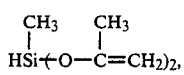

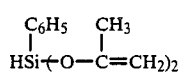

and the like, and an organosiloxane compound represented by General Formula:

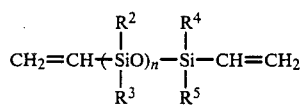 (III)

wherein R², R³, R⁴ and R⁵ are as defined above, for example,

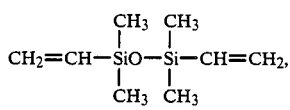

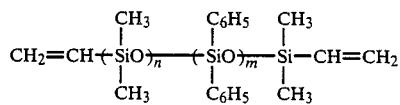

wherein m and n each are an integer of 0 or more,

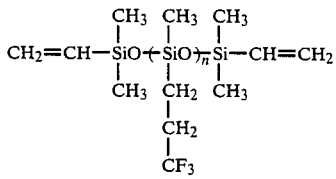

wherein n is an integer of 0 or more, and the like, are subjected to addition reaction by heating in the presence of a platinum catalyst.

In this instance, the hydrogen silane represented by Formula (II) may preferably be used in an amount of 0.8 to 2 mols per mol of the vinyl group contained in the organopolysiloxane compound represented by Formula (III). The platinum catalyst may preferably be used generally in an amount of $1.0 \times 10^{-10}$ to 0.1 mol, particularly preferably in an amount of $1.0 \times 10^{-5}$ to 0.01 mol, in terms of platinum, per mol of the vinyl group contained in the organopolysiloxane compound represented by Formula (III). The reaction may preferably be carried out at a temperature of about 40° C. to 150° C., particularly preferably 60° to 120° C. The platinum catalysts to be used may include, for example, chloroplatinic acid, etc. If necessary, the above reaction may be carried out with use of a solvent such as benzene, toluene and xylene.

Another process for synthesizing the compound represented by Formula (I) is a process in which a vinyl silane represented by General Formula:

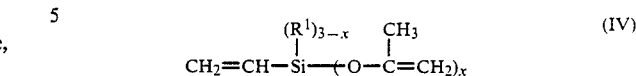 (IV)

wherein R¹ and x are as defined above, for example,

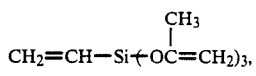

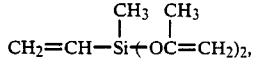

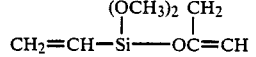

and the like, and a hydrogen-terminated organopolysiloxane compound represented by General Formula:

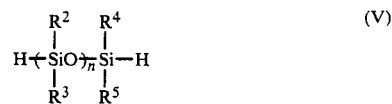 (V)

wherein R², R³, R⁴ and R⁵ are as defined above, for example,

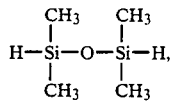

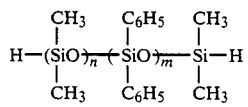

and the like, are subjected to addition reaction in the presence of the aforesaid platinum catalyst. In this instance, the vinyl silane represented by Formula (IV) may preferably be used in an amount of 0.8 to 2 mols per mol of the silicon-bonded hydrogen atom of the organopolysiloxane compound represented by Formula (V), and the platinum catalyst may preferably be used in an amount of $1.0 \times 10^{-10}$ to 1.0 mol, particularly preferably $1.0 \times 10^{-5}$ to 0.01 mole per mol of the silicon-bonded hydrogen atom of the organopolysiloxane compound represented by Formula (V). The reaction may preferably be carried out at a temperature of 40° to 150° C., particularly preferably 60° to 120° C. Also in this process, if necessary, the reaction may be carried out with use of a solvent such as benzene, toluene and xylene.

The organosilicon compound represented by Formula (I) of this invention can be utilized for various purposes. That is, for example, an organopolysiloxane containing two or more of mercapto groups in a molecule, for example,

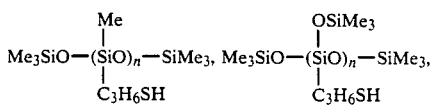

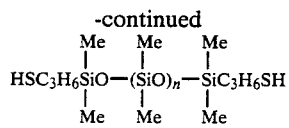

wherein n is an integer of 1 or more, or the like and a photosensitizer may be added to the organosilicon compound of this invention to obtain an ultraviolet curable silicone composition. Also, an organopolysiloxane containing two or more of silicon-bonded hydrogen atom

in its molecule and a platinum catalyst may be added to obtain an addition reaction type room temperature curable silicone composition. A curing catalyst for moisture curing may be added to obtain a condensation type room temperature curable silicone composition. Thus, the organosilicon compound of this invention is useful as a starting material for various silicone compositions.

EXAMPLE

This invention will be described below in detail by Examples.

EXAMPLE 1

In a 1 lit. glass flask equipped with a stirrer, a reflux device and a thermometer, 120 g of divinyltetramethyldisiloxane, 200 g of toluene and 1 g of an isopropyl alcohol solution of chloroplatinic acid (platinum content: 2% by weight) were added, and the temperature was raised to 100° C. To the resulting reaction mixture, 270 g of methyldiisopropenyloxysilane was dropwise added over a period of 1 hour. After the addition, the reaction mixture was kept at 100° C. to carry out the reaction for 2 hours. This reaction mixture was distilled under reduced pressure to obtain 168 g (yield: 52%) of a fraction which is colorless and transparent and has a refractive index ($n_D^{25}$) of 1.41 and a boiling point of 154° C. (under a reduced pressure of 2 mmHg). Analytical results of this compound are shown below:

$^1$H—NMR: δ (ppm) 0.1(s, Si—CH$_3$ 18H); 0.2(d, Si—CH$_2$—4H); 0.6(d, Si—CH$_2$—4H); 1.8(s, C—CH$_3$ 12H); 4.1(q, C=CH$_2$ 8H).

IR spectrum: As shown in FIG. 1. C=C 1640 cm$^{-1}$ Si—C 2950 cm$^{-1}$

| | Elementary analysis: (%) | | |
|---|---|---|---|
| | C | H | Si |
| Found: | 52.8 | 9.1 | 22.2 |
| Calculated*: | 52.53 | 9.21 | 22.33 |

(*: as Si$_4$C$_{22}$H$_{46}$O$_5$)

From the above results, the compound obtained was confirmed to be a compound represented by the following formula:

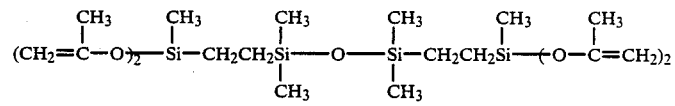

EXAMPLE 2

In the same manner as in Example 1, 18.6 g of divinyltetramethylsiloxane and 40 g of tripropenyloxysilane were reacted to obtain 21.1 g (yield: 36%) of a fraction which is colorless and transparent and has a refraction index ($n_D^{25}$) of 1.41 and a boiling point of 110° C. (under reduced pressure of 1 mmHg). Analytical results of this compound are shown below:

$^1$H—NMR: δ (ppm) 1.0(s, Si—CH$_3$ 12H); 0.2(s, Si—CH$_3$ 4H); 0.7(s, Si—CH$_2$ 4H); 1.9(s, C—CH$_3$ 18H); 4.1(d, C=CH$_2$ 12H).

Figure 2:
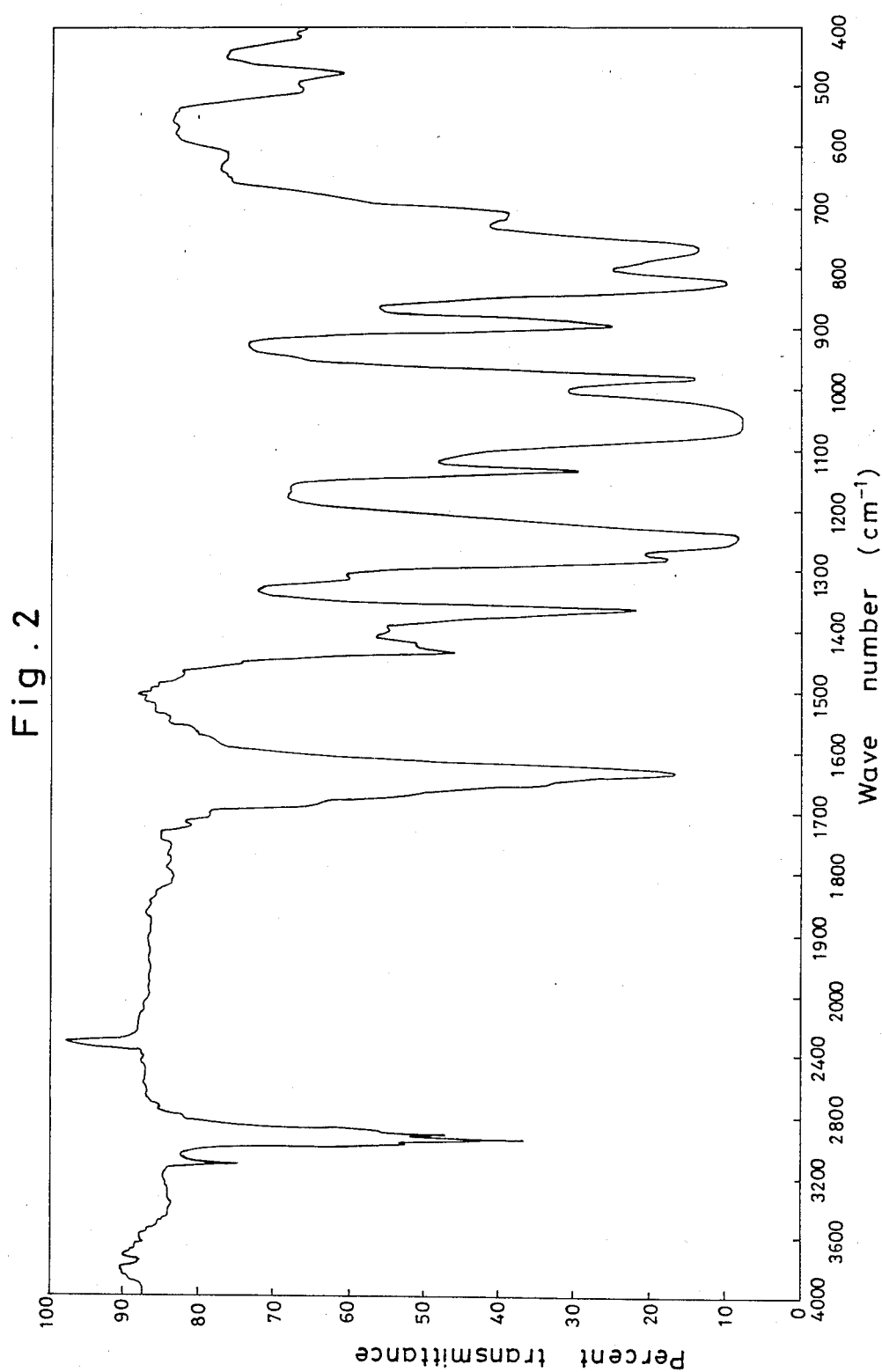

IR spectrum: As shown in FIG. 2. C=C 1640 cm$^{-1}$ Si—C 2950 cm$^{-1}$

| | Elementary analysis: (%) | | |
|---|---|---|---|
| | C | H | Si |
| Found: | 53.5 | 8.4 | 19.0 |
| Calculated*: | 53.19 | 8.58 | 19.13 |

(*: as Si$_4$C$_{26}$H$_{50}$O$_7$)

From the above results, the compound obtained was confirmed to be a compound represented by the following formula:

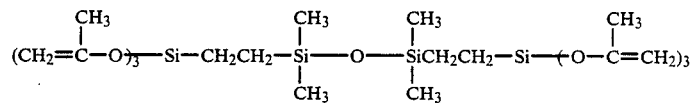

EXAMPLE 3

Figure 3:
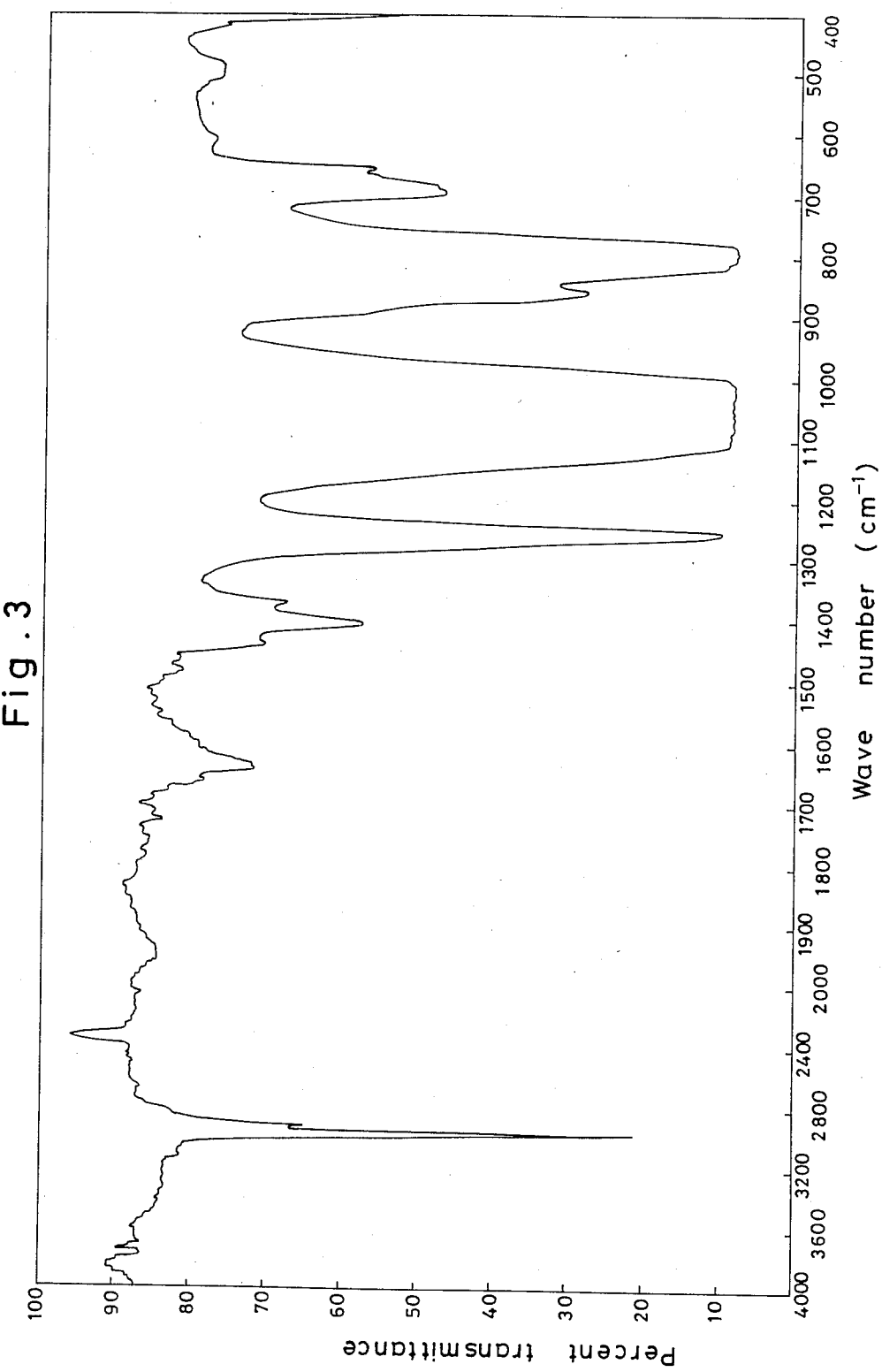

In a 5 lit. glass flask equipped with a stirrer, an ester adapter reflux device and a thermometer, 3,000 g of α,ω-divinyl polydimethylsiloxane having a viscosity of 110 cSt(25° C.) and 1,000 g of toluene were placed, and the content was heated under reflux to effect removal of water, followed by cooling to room temperature. To the mixture in the flask, 0.5 g of an isopropyl alcohol solution of chloroplatinic acid (platinum content: 2% by weight) and 170 g of methyldiisopropenyloxysilane were added, and the temperature was raised to 100° C, at which the reaction was carried out for 2 hours. The reaction mixture was placed under reduced pressure to remove toluene. As a result, there was obtained 2970 g (yield: 90%) of a colorless and transparent liquid having viscosity of 130 cSt(25° C.), a refraction index ($n_D^{25}$) of 1.41 and specific gravity of 0.974. Analytical results of this compound are shown below:

IR spectrum: As shown in FIG. 3. C=C 1640 cm$^{-1}$ Si—C 2950 cm$^{-1}$

Isopropenoxy group equivalent (mol/100 g): Found: 0.066 Calculated: 0.069

Based on the above, this compound was confirmed to be a compound whose molecular formula on average is represented by the following formula:

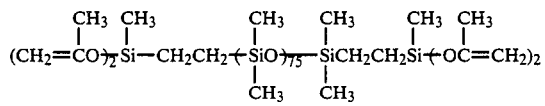

We claim:

1. An organosilicon compound represented by General Formula (I):

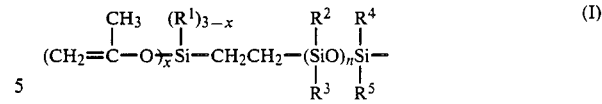

wherein $R^1$, $R^2$, $R^3$, $R^4$, $R^5$ and $R^6$ may be the same or different, and each represent a substituted or unsubstituted monovalent hydrocarbon group, x and y each represent an integer of 1 to 3, and n is an integer of 0 or more.

2. The organosilicon compound according to claim 1, wherein $R^1$, $R^2$, $R^3$, $R^4$, $R^5$ and $R^6$ are selected from lower alkyl groups having 1 to 3 carbon atoms and phenyl group, and n is an integer of 0 to 2,000.

3. The organosilicon compound according to claim 2, wherein $R^1$, $R^2$, $R^3$, $R^4$, $R^5$ and $R^6$ each is a methyl group and n is an integer of 1 to 1,000.

* * * * *